United States Patent [19]

Kurosawa et al.

[11] Patent Number: 4,950,380
[45] Date of Patent: Aug. 21, 1990

[54] LIMITING CURRENT-TYPE OXYGEN SENSOR

[75] Inventors: Hideyuki Kurosawa; Kazuhiro Takahashi; Yukio Nakanouchi, all of Kumagaya, Japan

[73] Assignee: Kabushiki Kaisha Riken, Tokyo, Japan

[21] Appl. No.: 388,670

[22] Filed: Aug. 1, 1989

[51] Int. Cl.$^5$ .............................................. G01N 27/41
[52] U.S. Cl. ................................. 204/406; 204/410; 204/412; 204/425
[58] Field of Search ................. 204/425, 410, 412, 1 S

[56] References Cited

U.S. PATENT DOCUMENTS

4,666,566  5/1987  Mizutani et al. ................. 204/1 T

Primary Examiner—G. L. Kaplan
Attorney, Agent, or Firm—Brumbaugh, Graves, Donohue & Raymond

[57] ABSTRACT

A limiting current-type oxygen sensor including (a) a pair of oxygen ion-permeable substrates made of a zirconia solid electrolyte; (b) at least one diffusion pore provided in at least one of the substrates, which extends substantially along the thickness of the substrate for causing oxygen diffusion through the diffusion pore to be a rate-determining step; (c) a sealing member for fixing the pair of substrates such that a closed chamber is defined between the substrates; and (d) a pair of porous electrodes provided on both outer and inner surfaces of each electrode.

4 Claims, 4 Drawing Sheets

LIMITING CURRENT-TYPE OXYGEN SENSOR

BACKGROUND OF THE INVENTION

The present invention relates to a limiting current-type oxygen sensor utilizing a zirconia solid electrolyte as an oxygen ion-permeable solid electrode, and more particularly to an oxygen sensor suitable for detecting an oxygen-depleted state in a relatively low temperature environment, particularly in working environment such as construction sites, in tanks, etc.

As miniature, high-sensitivity oxygen sensors, limiting current-type oxygen sensors utilizing a zirconia solid electrolyte as an oxygen ion-permeable means have conventionally been known.

The zirconia solid electrolyte is, as is well known, a ceramic of $ZrO_2$ (zirconia) containing CaO (calcia) or $Y_2O_3$ (yttria), etc. as a stabilizer in the form of a solid solution. This zirconia solid electrolyte shows a high oxygen ion permeability at a constant voltage when heated to 350° C. or higher. In other words, in an atmosphere containing oxygen, the zirconia solid electrolyte can selectively permit oxygen to pass therethrough. This solid electrolyte-type sensor can detect oxygen concentration in a gas being measured, by utilizing peculiar characteristics of such solid electrolyte.

In addition, the zirconia solid electrolyte has excellent heat resistance, corrosion resistance, thermal shock resistance, etc. Utilizing such advantages, the oxygen sensor made of a zirconia solid electrolyte is widely used for controlling combustion in boilers and furnaces, controlling air-fuel ratios and setting optimum conditions for cleaning exhaust gas in internal engines of automobiles, etc. and further detecting an oxygen-depleted state in such working environments as construction sites, in tanks, etc.

Solid electrolyte-type sensors utilized in such wide applications are generally classified into an oxygen concentration cell-type and an electrochemical pumping-type.

The oxygen concentration cell-type sensor generally has a structure in which a substrate made of a zirconia solid electrolyte is provided with porous Pt electrodes on both surfaces thereof. One electrode is in contact with a gas being measured while the other electrode is in contact with a reference gas having a known oxygen concentration, for instance, the air. By this structure, an oxygen concentration cell is formed, and the measurement of electromotive force of this oxygen concentration cell can lead to the detection of the oxygen concentration of the gas being measured.

On the other hand, the electrochemical pumping-type sensor is constructed such that the oxygen concentration of the gas being measured can be detected by utilizing an electrochemical pumping function. This electrochemical pumping function means that when voltage is applied to an oxygen ion-permeable zirconia solid electrolyte, the oxygen in the gas being measured is reduced to oxygen ions by a negative electrode, and these oxygen ions move through the solid electrolyte to a positive electrode, where they are oxidized to oxygen again, and it is discharged outside.

As a typical sensor utilizing the above electrochemical pumping function, a limiting current-type oxygen sensor is disclosed in Japanese Patent Publication No. 59-26895. This limiting current-type oxygen sensor will be explained as a first type sensor referring to FIG. 5.

Figure 5:
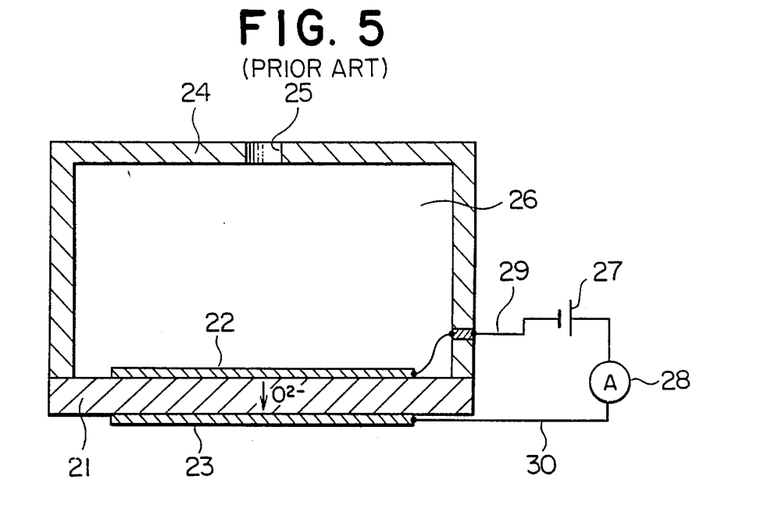
FIG. 5 is a cross-sectional view showing the conventional oxygen sensor of the first type as a limiting current-type oxygen sensor.

In FIG. 5, the sensor comprises a planar oxygen ion-permeable solid electrolyte 21 provided with a porous internal electrode (negative electrode) 22 and a porous external electrode (positive electrode) 23 on both surfaces thereof. Fixed to the solid electrolyte 21 on the side of the internal electrode 22 is a gas diffusion adapter 24 provided with a gas diffusion pore 25 having a desired pore diameter for permitting an oxygen gas to go into an internal chamber 26 defined by the solid electrolyte 21 and the gas diffusion adapter 24. 27 denotes a DC power supply, and 28 denotes a current measurement circuit, one terminal of which is connected to a positive terminal of the DC power supply 27. 29 denotes a lead wire for connecting the internal electrode 22 to the negative terminal of the DC power supply 27, and 30 denotes a lead wire for connecting the external electrode 23 to the current measurement circuit 28.

In the limiting current-type oxygen sensor having the above structure, when a certain voltage is applied to the solid electrolyte 21 by the DC power supply 27 with the internal electrode 22 and the external electrode 23 biased negatively and positively, respectively, oxygen in the internal chamber 26 is electrochemically pumped to the outside through the solid electrolyte 21. In this process, the amount of oxygen diffused through the gas diffusion pore 25 from outside into the internal chamber 26 is controlled by the rate of oxygen diffusion through the gas diffusion pore 25, so that the amount of oxygen ions moving in the solid electrolyte 21 is kept constant. As a result, a constant limiting current proportional to the oxygen concentration in the gas being measured flows in the electric current measurement circuit 28. Thus, the oxygen concentration in the gas being measured can be known from the limiting current obtained by applying a constant voltage.

The limiting current obtained in such a process varies depending upon the size of the gas diffusion pore 25, namely an opening ratio (an area of opening/length of pore) of the gas diffusion pore 25. When the opening ratio is decreased by decreasing the pore diameter of the gas diffusion pore 25, the rate of the process is more controlled by oxygen diffusion through the gas diffusion pore 25, leading to the decrease in limiting current.

On the other hand, when the opening ratio is increased by increasing the pore diameter of the gas diffusion pore 25, the rate of process is less controlled by oxygen diffusion through the gas diffusion pore 25, leading to the increase in a limiting current. Apart from the influence by the area of the electrode, it is generally satisfied that the smaller the limiting current, the smaller the voltage applied to obtain such limiting current.

Figure 6:
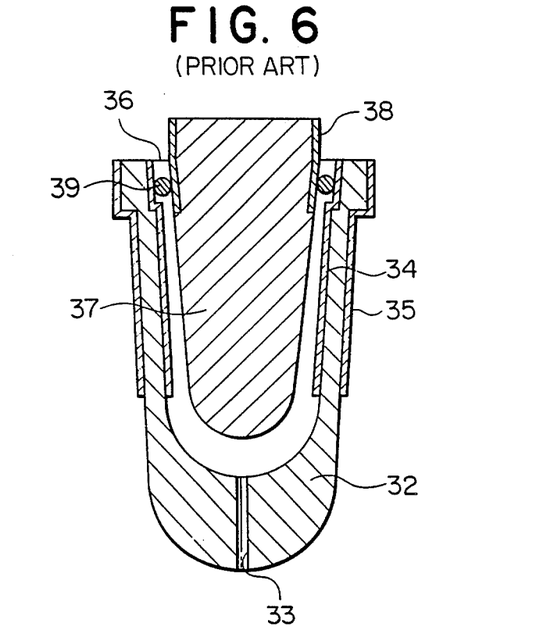
FIG. 6 is a cross-sectional view showing the conventional oxygen sensor of the second type as a limiting current-type oxygen sensor.

Japanese Patent Laid-Open No. 59-88653 discloses as a second type a limiting current-type oxygen sensor as shown in FIG. 6.

In FIG. 6, the oxygen sensor comprises a tubular oxygen ion-permeable solid electrolyte container ($ZrO_2 + Y_2O_3$) 32 provided with a gas diffusion pore 33 in a center portion of the bottom of the container 32. This solid electrolyte container 32 is provided, on both upper inner and outer surfaces, with a negative electrode 34 and a positive electrode 35. A top opening portion of the container 32 is lined with a metallized layer 36. 37 denotes an elongated lid member made of the same material as that of the container 32, an upper side wall of which is coated with a metallized layer 38. The solid electrolyte container 32 and the lid member 37 are in contact with each other between the metallized layers 36 and 38 via an annular seal member 39.

In this oxygen sensor of the second type, oxygen in a gas being measured is diffused from outside (a system to be measured) to a cavity defined by the solid electrolyte container 32 and the lid member 37 via the gas diffusion pore 33, and oxygen diffusion through the gas diffusion pore 33 determines a total oxygen diffusion rate of this sensor. Accordingly, a constant limiting current in proportion to the oxygen concentration of the gas being measured flows between the negative electrode 34 and the positive electrode 35, thereby enabling the detection of oxygen concentration.

Further, a limiting current-type oxygen sensor is known by Japanese Patent Laid-Open No. 57-48648.

In addition to the above limiting current-type oxygen sensors, oxygen sensors having electrochemical pumping mechanisms and oxygen concentration detection elements are also known.

Figure 7:
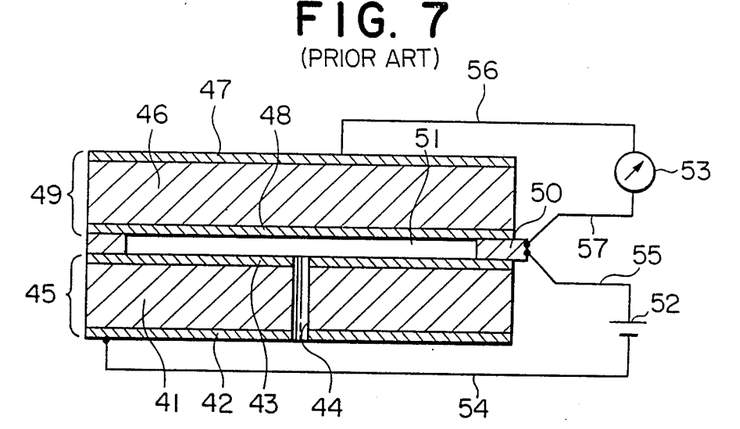
FIG. 7 is a cross-sectional view showing the conventional oxygen sensor of the third type as a limiting current-type oxygen sensor.

Japanese Patent Laid-Open No. 57-97439 discloses as a third type an oxygen sensor shown in FIG. 7.

In FIG. 7, the oxygen sensor comprises an oxygen pumping element 45 constituted by a solid electrolyte 41 having a fine pore 44 substantially in a center thereof and electrodes 42, 43 formed on both surfaces of the solid electrolyte 41, and an oxygen detection element (oxygen concentration cell) 49 constituted by a solid electrolyte 46 and electrodes 47, 48 formed on both surfaces of the solid electrolyte 46. The oxygen pumping element 45 and the oxygen detection element 49 are fixed to each other via an annular conductive member 50 such that their planar surfaces are opposite to each other. An internal chamber 51 is defined by the electrodes 43, 48 and the annular conductive member 50. 52 denotes a DC power supply, 53 denotes an electromotive force meter and 54-57 denote lead wires. Incidentally, contact portions of the oxygen pumping element 45 and the oxygen detection element 49 may be sealed with a glass material.

When a constant voltage is applied to the oxygen pumping element 45 by the DC power supply 52, the internal chamber 51 is filled with a reference gas (air) by an oxygen pumping function. In this state, when the electrode 47 of the oxygen detection element 49 is brought into contact with a gas to be measured, an oxygen concentration cell is formed, whereby an electromotive force in proportion to a ratio of the oxygen concentration of the reference gas to the oxygen concentration of the gas being measured can be obtained from the element 49. The oxygen concentration of the gas being measured can be known by measuring this electromotive force by an electromotive force meter 53.

Japanese Patent Laid-Open No. 58-210560 discloses as a fourth type an oxygen sensor which has a similar structure to that shown in FIG. 6. Namely, the oxygen sensor of the fourth type comprises a tubular oxygen ion-permeable ceramic element provided with a gas diffusion pore in its bottom and two pairs of electrodes opposite to each other via the gas diffusion pore on both inner and outer surfaces of the bottom, and a ceramic lid member for sealing an open end of the tubular oxygen ion-permeable ceramic element, thereby providing an internal chamber therebetween. One pair of electrodes and a ceramic element portion therebetween function as a pumping cell, and another pair of electrodes and a ceramic element portion therebetween function as a sensor cell (oxygen concentration cell). The principle of oxygen concentration detection in the oxygen sensor of the fourth type is essentially the same as in that of the third type.

Figure 8:
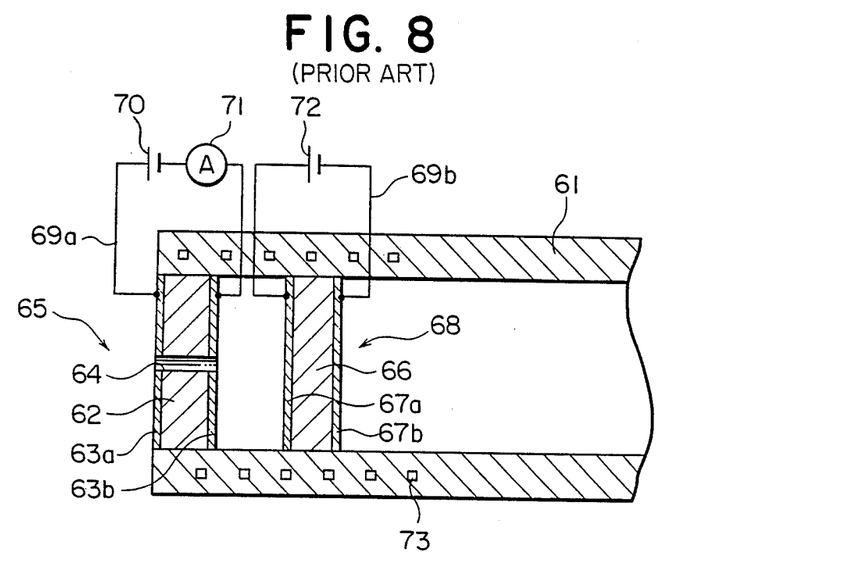
FIG. 8 is a cross-sectional view showing the conventional oxygen sensor of the fifth type as a limiting current-type oxygen sensor.

Japanese Patent Laid-Open No. 60-24445 discloses as a fifth type an automobile oxygen sensor as shown in FIG. 8.

In FIG. 8, the oxygen sensor comprises a cylindrical ceramic member 61 and a lean sensor (limiting current-type oxygen sensor capable of detecting oxygen only in a lean range of an air-fuel ratio) 65 attached to one open end of the cylindrical member 61. The lean sensor 65 is constituted by an oxygen ion-permeable solid electrolyte 62 having a gas diffusion pore 64 in its center, and electrodes 63a, 63b formed on both surfaces of the solid electrolyte 62. The oxygen sensor also comprises an oxygen pump 68 fixed in the cylindrical member 61 such that an internal chamber is defined between the lean sensor 65 and the oxygen pump 68. The oxygen pump 68 is constituted by an oxygen ion-permeable solid electrolyte 66 and electrodes 67a, 67b formed on both surfaces of the solid electrolyte 66. 69a and 69b denote lead wires, 70 and 72 denote stabilized DC power supplies. 71 denotes a current measurement circuit, and 73 denotes a heater contained in the cylindrical member 61.

In this oxygen sensor of the fifth type having the above structure, the internal chamber is filled with oxygen having a known concentration pumped by the oxygen pump 68, and a gas introduced through the gas diffusion pore 64. Accordingly, even when the gas being measured is in a rich state of an air-fuel ratio (oxygen-depleted state), the internal chamber is in a lean state (oxygen excess state). Therefore, a limiting current obtained by the lean sensor 65 can lead to the detection of oxygen concentration in the gas being measured.

However, the above-described solid electrolyte-type oxygen sensors have various problems as mentioned below.

In the case of the oxygen concentration cell-type sensor, since the reference gas is required as its essential element, the sensor volume is inevitably large, consuming much electric energy.

In the cases of the electrochemical pumping-type sensors exemplified by the first and second types, the reference gas is not needed, making it possible to miniaturize the sensor itself as compared to the above-described oxygen concentration cell-type sensor. However, it still suffers from the following peculiar problems. That is, to achieve the rate determination by oxygen diffusion, the adapter 24 having a gas diffusion pore 25 is needed as an additional element in the first type, and the lid member 37 and the seal member 39 are needed in the second type. Accordingly, these electrochemical pumping-type sensors have relatively complicated structures because of increased numbers of parts.

In the cases of the oxygen sensors having the electrochemical pump and the oxygen concentration cell exemplified by the third and fourth types, and the oxygen sensor of the fifth type having the electrochemical pump and the lean sensor, they are disadvantageous in complicated structure. In addition, constituent elements such as the electrochemical pump, the oxygen concentration cell and the lean sensor should be quality-controlled, but the control of their quality is rather difficult. As a result, unevenness in quality inevitably occurs among the sensors having such elements.

Also, in the above-described electrochemical pumping-type sensors, to increase response velocities by decreasing the heat capacities of the overall sensors, the sensors themselves should be miniaturized. In this case, the gas diffusion pores inevitably have reduced diameters in the above structures. However, in the electrochemical pumping-type sensors, the gas diffusion pores are directly exposed to a gas being measured. Accordingly, the fine diffusion pores are likely to be clogged with dust in the gas being measured, leading to the deterioration of their function as sensors.

OBJECT AND SUMMARY OF THE INVENTION

An object of the present invention is, therefore, to provide a limiting current-type oxygen sensor having a structure suitable for miniaturization, which is excellent in stability and enjoys a long service life.

The present invention provides the limiting current-type oxygen sensor comprising (a) a pair of oxygen ion-permeable substrates made of a zirconia solid electrolyte: (b) at least one diffusion pore provided in at least one of the substrates, which extends substantially along the thickness of the substrate for causing oxygen diffusion therethrough to be a rate-determining step: (c) a sealing member for fixing the pair of substrates such that a closed internal chamber is defined: and (d) a pair of porous electrodes provided on both outer and inner surfaces of each substrate, an opening of the diffusion pore being covered by the porous electrode provided on an outer surface of the substrate having the diffusion pore.

DETAILED DESCRIPTION OF THE INVENTION

Figure 1:
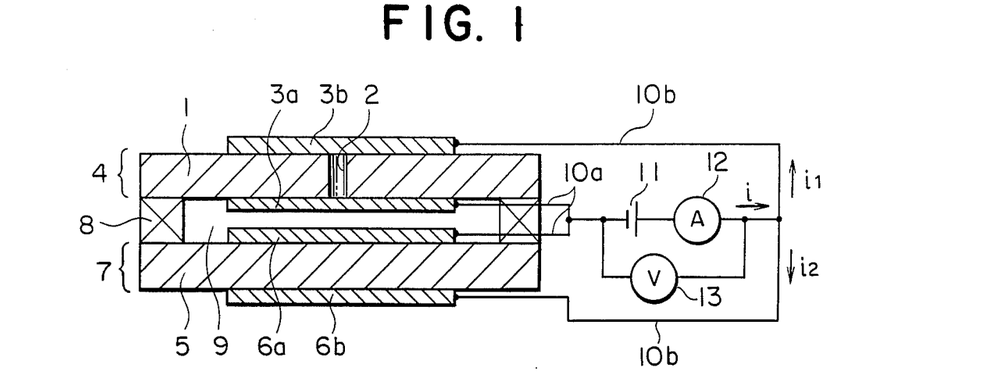
FIG. 1 is a cross-sectional view showing the oxygen sensor according to one embodiment of the present invention.

Referring to FIG. 1, the oxygen sensor according to one embodiment of the present invention comprises first and second oxygen ion-permeable, planar substrates 1, 5 both made of a zirconia solid electrolyte, and one of the substrates, for instance, the first substrate 1 is provided with a diffusion pore 2 extending along the thickness of the substrate 1 substantially in its center portion to achieve rate determination by oxygen diffusion.

The zirconia solid electrolyte constituting the first and second substrates 1, 5 is, for instance, made of $ZrO_2$ in which at least one of $Y_2O_3$, MgO, $Yb_2O_3$, etc. is dissolved as a stabilizer. In FIG. 1, only one diffusion pore 2 is provided in the first substrate 1, but a plurality of diffusion pores may be provided, or both first and second substrates 1, 5 may be provided with diffusion pores.

To achieve the miniaturization of the oxygen sensor and the operation of the oxygen sensor at a low temperature, particularly at 350°-500° C., the first and second substrates 1, 5 preferably have a thickness of 0.1-0.5 mm, and the diffusion pore 2 preferably has a pore size of 10-50 $\mu$m.

On inner and outer surfaces of the first substrate 1, a first porous internal electrode 3a, and a first porous external electrode 3b are provided in areas opposite to each other via the substrate 1 including the opening of the diffusion pore 2 with a predetermined width from the periphery of the substrate 1.

Similarly, on inner and outer surfaces of the second substrate 5, a second porous internal electrode 6a and a second porous external electrode 6b are provided in areas opposite to each other via the second substrate 5 except for their peripheral areas of a predetermined width.

Incidentally, the first internal electrode 3a, which is not directly exposed to a gas to be measured and so is less likely to be affected by dust, may be located such that it does not cover an opening of the diffusion pore 2. The same is true in a case where a plurality of diffusion pores are provided in the first and second substrates 1, 5.

In order that the first internal and external electrodes 3a, 3b and the second internal and external electrodes 6a, 6b function as catalytically active electrodes, they are preferably made of metal materials such as Pt, Pd, Ag, Rh, Ir, etc. or mixed materials of these metal materials and at least one oxygen ion-permeable oxide material, and particularly Pt or a mixed material of Pt and $ZrO_2$ is preferable.

These electrodes 3a, 3b, 6a, 6b should be porous. In this case, the electrodes preferably have an average particle size of 1-3 $\mu$m and an average pore size of 0.1-5 $\mu$m and a porosity of 70-85%.

In a case where these factors are within the above ranges, the external electrode 3b formed on the substrate 1 having the diffusion pore 2 functions as a filter for dust contained in a gas being measured. Because of this function, an effective diameter of the diffusion pore 2 does not change, and the rate-determining function of the diffusion pore 2 can be maintained.

This oxygen sensor is constituted as a combination of two sensor elements. That is, 4 denotes a first sensor element constituting a main part of the oxygen sensor, which comprises the first substrate 1 having the diffusion pore 2 and the first internal electrode 3a and the first external electrode 3b. 7 denotes a second sensor element which comprises the second substrate 5 and the second internal electrode 6a and the second external electrode 6b. The second sensor element 7 may also be provided with a diffusion pore.

The first and second sensor elements 4, 7 are disposed opposite to each other via a sealing member 8 such that the first and second internal electrodes 3a, 6a are sealed and an internal chamber 9 is defined therebetween. For instance, in the case of FIG. 1, the first and second substrates 1, 5 are fixed to each other by an annular sealing spacer as a sealing member 8 in peripheral areas of the inner surfaces of the substrates 1, 5 to define the internal chamber 9. Incidentally, the sealing member 8 is made of glass materials to substantially isolate the internal chamber 9 from the outside atmosphere.

In the oxygen sensor thus constructed according to one embodiment of the present invention, the first and second substrates 1, 5 made of the zirconia solid electrolyte function as oxygen ion-permeable media for effecting oxygen pumping in the operation of the oxygen sensor. At least one diffusion pore 2 provided in at least one of the first and second substrates 1, 5 (one diffusion pore 2 in the first substrate 1 in FIG. 1) functions as a rate-determining means, which controls the rate of oxygen supply from the outside (a gas to be measured) to the internal chamber 9. Namely, the oxygen supply rate is determined by oxygen diffusion through the diffusion pore 2.

Accordingly, in the embodiment shown in FIG. 1, the first substrate 1 having the diffusion pore 2 has both functions as an oxygen ion-permeable medium and as a rate-determining means. On the other hand, the second substrate 5 having no diffusion pore functions only as an oxygen ion-permeable medium.

Further, since the first internal and external electrodes 3a, 3b are porous, they function as catalytically active electrodes for activating the electrode reaction, whereby interfaces between the first substrate 1, these electrodes 3a, 3b and oxygen are enlarged, resulting in the increase of oxygen pumping efficiency. The second porous internal and external electrodes 6a, 6b also function as catalytically active electrodes.

Incidentally, in the embodiment of FIG. 1, since both openings of the diffusion pore 2 provided in the substrate 1, are covered by the first external electrode 3b and the first internal electrode 3a, the electrodes 3a, 3b function as filters for the diffusion pore 2.

In a case where the diffusion pore 2 is provided also in the second substrate 5, the second internal and external electrodes 6a, 6b may have the same structures as the first internal and external electrodes 3a, 3b. Accordingly, the electrodes 6a, 6b can function as filters for the diffusion pore like the electrodes 3a, 3b.

Further, since the first and second sensor elements 4, 7 are fixed to each other by means of the sealing member 8 such that the first and second internal electrodes 3a, 6a are sealed and the internal chamber 9 is defined between the electrodes 3a and 6a, the atmosphere in this internal chamber 9 is substantially isolated from the gas atmosphere being measured.

For these reasons, the first and second sensor elements 4, 7 function not only as electrochemical oxygen pumping means and rate-determining means but also as means for sealing the first and second internal electrodes 3a, 6a.

As described above, the oxygen sensor according to one embodiment of the present invention utilizes the first and second substrates 1, 5 to define the internal chamber 9 and provides these substrates 1, 5 with porous electrodes 3a, 3b, 6a, 6b. Because of this structure, as compared to the conventional oxygen sensors, the electrode area can be substantially increased for the same sensor size. Since the interface areas between three phases of the substrates 1, 5, the electrodes 3a, 3b, 6a, 6b and oxygen are doubled as compared to the oxygen sensor having one substrate, the amount of oxygen pumped at a predetermined input voltage can also be doubled.

Therefore, in the same diffusion pore diameter and the same limiting current, the input voltage for oxygen pumping can be made sufficiently lower in the oxygen sensor according to one embodiment of the present invention than in the conventional oxygen sensors.

Specific examples of the present invention will be described below in detail.

EXAMPLE 1

In FIG. 1, 1 and 5 respectively denote first and second substrates made of a zirconia solid electrolyte of $ZrO_2$ (zirconia) containing $Y_2O_3$ (yttria) as a stabilizer. As is well known, when heated to 350° C. or higher in a state where a certain voltage is applied, the zirconia solid electrolyte shows oxygen ion permeability, thereby enabling oxygen pumping.

The first and second substrates made of the zirconia solid electrolyte are both shaped in a dense, planar form with a sufficiently small porosity. In the case of this Example, the thickness of each substrate is 0.2 mm.

2 denotes a diffusion pore provided in the first substrate 1 in its center, which extends along the thickness of the first substrate 1 with a pore diameter of 15 $\mu$m. In this Example, the diffusion pore 2 is provided only in the first substrate 1, so that the first substrate 1 has a function as an oxygen ion-permeable means and a rate-determining means. In this case, since the second substrate 5 does not have a diffusion pore, it functions only as an oxygen ion-permeable means.

The first internal and external electrodes 3a, 3b, are respectively formed on the inner and outer surfaces of the first substrate 1 in their areas opposite to each other including both openings of the diffusion pore 2 with a certain space between their peripheries and those of the first substrate 1.

The second internal and external electrodes 6a, 6b are formed on the inner and outer surfaces of the second substrate 5 in their areas opposite to each other, except for their peripheral areas of a predetermined width. And their electrode areas are substantially the same as those of the first internal and external electrodes 3a, 3b.

These first porous internal and external electrodes 3a, 3b and the second porous internal and external electrodes 6a, 6b function as catalytically active electrodes for activating the electrode reaction. In this Example, they are constituted by Pt electrodes. These Pt electrodes 3a, 3b, 6a, 6b are formed by coating the first and second substrates 1, 5 in the above areas on their inner and outer surfaces with a conductive paste containing Pt powder having an average particle size of 0.1 $\mu$m, an organic binder and an organic solvent and then baking it in the air.

Incidentally, in FIG. 1, the first sensor element 4 constituting the oxygen sensor of this Example is constituted by the first substrate 1 having the diffusion pore 2 and the Pt electrodes 3a, 3b formed on both surfaces of the first substrate 1.

This first sensor element 4 shows an electrochemical oxygen pumping function, a rate-determining function, and a sealing function for sealing the Pt electrodes 3a, 6a.

The second sensor element 7 comprises the second substrate 5 having no diffusion pore and the Pt electrodes 6a, 6b formed on both surfaces of the substrate 5. It shows an electrochemical oxygen pumping function and a sealing function.

Here, the electrode area S is a sum of a total area $S_1$ of the Pt electrodes 3a, 3b opposite to each other on the first substrate 1, and a total area $S_2$ of the Pt electrodes 6a, 6b opposite to each other on the second substrate 5. In this Example, since $S_1 = S_2$, $S = 2S_1$.

As is clear from the above, in this Example, since the electrode area S for activating the electrode reaction is large on the first and second substrates 1, 5, interfaces between three phases of the first and second substrates (zirconia solid electrolyte) 1, 5, the Pt electrodes 3a, 3b, 6a, 6b and oxygen in the gas being measured are extremely large. Therefore, the oxygen pumping can be fully utilized.

Further, the porosity of the Pt electrodes 3a, 3b, 6a, 6b are determined by various factors such as their average particle size, average pore size and pore ratio, and these factors are adjusted with full reproducibility.

The average pore size of the electrodes is controlled to be less than the pore diameter (15 μm) of the diffusion pore 2, for instance, 4 μm. Accordingly, the Pt electrodes 3a, 3b can function not only as catalytically active electrodes but also as filters for the diffusion pore 2. Specifically speaking, when there is dust such as soot having a particle size larger than the average pore size of the Pt electrodes 3a, 3b, the dust does not clog the diffusion pore 2 because the Pt electrodes 3a, 3b effectively function as filters.

In fact, since the fine pores of the Pt electrodes 3a, 3b, 6a, 6b are mostly oval in cross section and have pore diameters of submicrons, they can function as filters against dust having a particle size equal to or smaller than the average pore size of the electrodes.

In addition, the Pt electrodes 3a, 3b, 6a, 6b are as porous as having a porosity of about 80% or so. Accordingly, even though part of the pores of the Pt electrodes are clogged with dust, sufficient diffusion of oxygen can be maintained through unclogged pores.

The average particle size of the Pt electrodes 3a, 3b, 6a, 6b are controlled to be fully smaller than the pore diameter (15 μm) of the diffusion pore 2, for instance, 3 μm. Accordingly, in the first substrate 1, particles constituting the Pt electrodes 3a, 3b do not directly clog the diffusion pore 2, and so the effective pore diameter of the diffusion pore 2 is kept unchanged. Because of this feature, together with the above porosity of the Pt electrodes 3a, 3b, the rate-determining function of the diffusion pore 2 is not affected by the Pt electrodes.

8 denotes a sealing means constituted by a sealing spacer made of glass, and the first sensor element 4 having the first substrate 1 and the second sensor element 7 having the second substrate 5 are fixed to each other in an opposite manner via this sealing spacer 8. This structure can be obtained by coating the inner surface of the first substrate 1 in an area outside the Pt electrode 3a with a glass paste for constituting the sealing spacer 8 of a predetermined width, and then fixing this to the inner surface of the second substrate 5 (a surface in which the Pt electrode 6a is formed). Incidentally, the glass paste may also be coated on an inner surface (a surface in which the Pt substrate 6a is formed) of the second substrate 5.

Because of the above structure, the first and second internal electrodes 3a, 6a are substantially isolated from the outside (the gas atmosphere to be measured) by the first and second sensor elements 4, 7 and the sealing spacer 8. Thus, the first and second sensor elements 4, 7 also function as sealing means.

As a result, an internal chamber 9 is defined between the first and second internal electrodes 3a and 6a. This internal chamber 9 has a small thickness and so a small volume.

The first and second external electrodes 3b, 6b are in direct contact with the gas to be measured while the first and second internal electrodes 3a, 6a are in contact with the gas being measured which is introduced into the internal chamber 9 through the diffusion pore 2.

11 denotes a stabilized DC power supply, and 12 denotes a current measurement circuit connected in series to a positive terminal of this power supply 11. 13 denotes a voltage measurement circuit connected in parallel to the power supply 11 and the current measurement circuit 12. 10a denotes lead wires for connecting negative terminals of the power supply 11 to the first and second internal electrodes 3a, 6a, and part of the lead wires penetrates through the sealing spacer 8 with full sealing. 10b denotes lead wires for connecting a terminal of the current measurement circuit 1 to the first and second external electrodes 3b, 6b.

Since the first and second substrates 1, 5 are as thin as 0.2 mm and since the internal chamber 9 of a small volume is provided between the first and second sensor elements 4, 7 having the first and second substrates 1, 5, the heat capacity of the oxygen sensor itself is sufficiently small.

Next, the operation of the oxygen sensor of this Example thus constituted will be explained below.

The first and second substrates 1, 5 are heated to a predetermined temperature of 350° C. or higher, and in this state, a predetermined voltage is applied between the Pt electrode 3a (negative electrode) and the Pt electrode 3b (positive electrode) and between the Pt electrode 6a (negative electrode) and the Pt electrode 6b (positive electrode) by the DC power supply 11.

The oxygen contained in the gas introduced into the internal chamber 9 is discharged through the first and second substrates 1, 5 by an electrochemical oxygen pumping function.

Specifically speaking, on the side of the first sensor element 4, the oxygen in the internal chamber 9 is reduced to oxygen ions in a three-phase interface between the porous Pt electrode 3a, the first substrate 1 and oxygen. The oxygen ions move through the biased first substrate 1 to reach the porous Pt electrode 3b, and in the three-phase interface between these oxygen ions, the first substrate 1 and the Pt electrode 3b, they are oxidized to an oxygen gas. The oxygen gas thus formed escapes outside through the porous Pt electrode 3b.

On the side of the second sensor element 7, too, the reduction of the oxygen in the three-phase interface on the Pt electrode 6a, the movement of the oxygen ions through the second substrate 5 and the oxidation of the oxygen ions in the three-phase interface on the Pt electrode 6b similarly take place, and the oxygen gas thus formed escapes outside through the porous Pt electrode 6b.

Once oxygen pumping takes place like this, the oxygen concentration in the internal chamber 9 decreases, whereby oxygen is supplemented by diffusion through the diffusion pore 2 from the outside gas atmosphere. However, since the diffusion process of oxygen is controlled by the oxygen diffusion through the diffusion pore 2, a constant amount of oxygen escapes from the internal chamber 9 through the first and second sensor elements 4, 7 by oxygen pumping. Because of this phenomenon, a constant limiting current i which is a sum of constant limiting currents $i_1$ and $i_2$ obtained separately from the first and second elements 4, 7, flows through the current measurement circuit 12. This limiting current i depends on the size of the diffusion pore 2, namely an opening ratio (area of opening/pore length) of the diffusion pore 2, because the oxygen diffusion rate is determined by the diffusion pore 2, and further it depends on the oxygen concentration of the gas being measured as a carrier source density.

Figure 3:
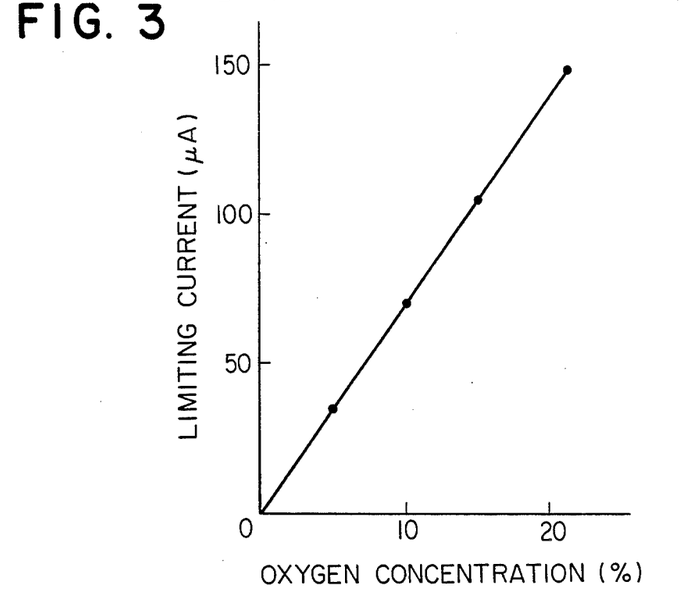
FIG. 3 is a graph showing the relation between the limiting current and the oxygen concentration in the oxygen sensor of Example 1.
Figure 4:
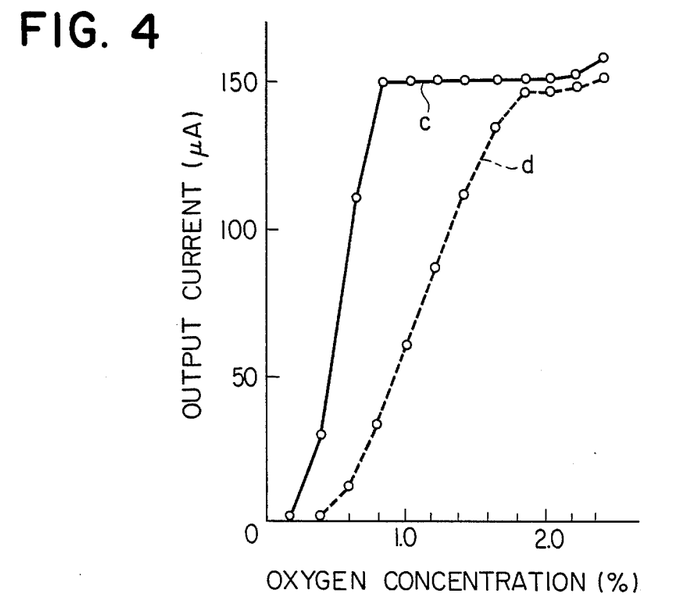
FIG. 4 is a graph showing the relation between the output current and the oxygen concentration in the oxygen sensor of Example 1 and the oxygen sensor having only one zirconia solid electrolyte substrate.

As described above, since the limiting current i has a constant level determined by the above factors, the input voltage can be made low in the detection of the limiting current i by increasing the electrode area to enhance oxygen pumping as in this Example. Such limiting current characteristics are shown in FIGS. 2–4.

Figure 2:
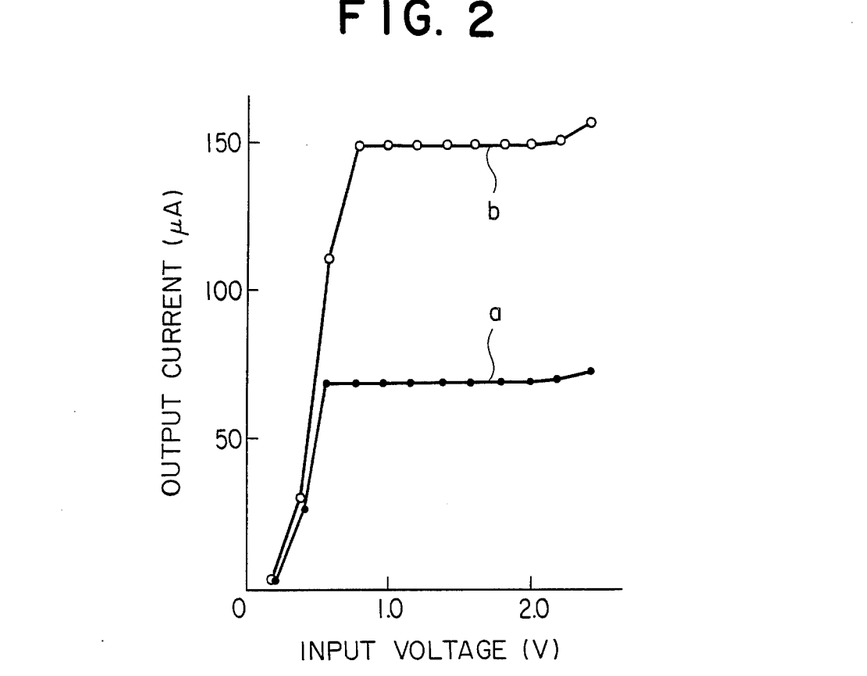
FIG. 2 is a graph showing the relation between output current and input voltage variable with oxygen concentration as a parameter in the oxygen sensor of Example 1.

FIG. 2 shows the dependency of output current on input voltage in the oxygen sensor in this Example. In FIG. 2, curves "a" and "b" are characteristic curves when oxygen concentrations are 10% and 21%, respectively. Incidentally, the heating temperature is 420° C.

As is clear from these curves "a" and "b", the higher the oxygen concentration in the gas being measured (curve "b"), the higher output current is obtained from the same input voltage. In the curves "a" and "b", at input voltage in such wide ranges as 0.6–2.2 V and 0.8–2.2 V. whose lower limits are both lower than 1.0 V, the output current is almost constant, showing no dependency on input voltage. Accordingly, in the cases of oxygen concentrations of 10% and 21%, the limiting current is respectively 70 $\mu$A and 150 $\mu$A.

In this case, the diffusion pore 2 has a pore diameter of 15 $\mu$m (opening ratio: $8.8 \times 10^{-4}$). If the pore diameter of the diffusion pore 2 is decreased to have a smaller opening ratio, the rate-determining level of the diffusion pore 2 is intensified, whereby the limiting current at each oxygen concentration decreases correspondingly. On the contrary, if the pore diameter of the diffusion pore 2 is increased to have a larger opening ratio, the rate-determining level is lowered, whereby the limiting current increases correspondingly.

FIG. 3 shows the dependency of the limiting current on the oxygen concentration at input voltage of 1.2 V and at 420° C. It is clear from FIG. 3 that even at a relatively small input voltage of 1.2 V, the limiting current changes almost linearly with the oxygen concentration of the gas being measured in a wide range including 0–21%. High sensitivity characteristics of the limiting current-type oxygen sensor is derived from this linearity between the limiting current and the oxygen concentration.

Next, FIG. 4 shows the limiting current characteristics of this Example together with those of the oxygen sensor having only one zirconia solid electrolyte substrate provided with a diffusion pore (simply referred to as "comparative sensor"), both at a heating temperature of 420° C. In FIG. 10, a curve "c" is a characteristic curve in this Example (corresponding to curve "b" in FIG. 2), and a curve "d" is a characteristic curve of the comparative sensor.

A main part of the comparative sensor having an active function composed of a substrate, a diffusion pore and porous electrodes has substantially the same construction as that of the first sensor element 4 of this Example. Specifically speaking, in the case of the comparative sensor, the substrate has a thickness of 0.2 mm, and the diffusion pore provided in this substrate has a pore diameter of 15 $\mu$m, and the electrode area is almost the same. Incidentally, a sealing plate made of $ZrO_2$ for defining the internal chamber has a thickness of 0.2 mm.

In FIG. 4, in the case of this Example shown by the curve "c", the limiting current (150 $\mu$A) is obtained when the input voltage is 0.8–2.2 V. Thus, the lower limit of the input voltage is as low as 0.8 V, and the limiting current is obtained in a wide range of the input voltage.

This appears to be due to the facts that the first and second substrates 1, 5 are used to define the internal chamber 9, that the electrode area is wide by forming electrodes on both substrates, and that this enables effective pumping of a certain amount of oxygen ions which is balanced by the amount of oxygen whose supply rate is controlled by the diffusion rate in the gas diffusion pore 2, even at a low input voltage.

Accordingly, in a case where the first and second substrates 1, 5 are made thin to miniaturize the sensor, the pore diameter of the diffusion pore 2 need not be reduced greatly, even if necessary. In this case, since the rate-determining function by oxygen diffusion through the gas diffusion pore 2 is weakened, the limiting current is increased. However, since the electrode area is large because of both substrates 1, 5, a large limiting current can be obtained at a relatively low input voltage.

On the other hand, in the comparative sensor shown by the curve "d", the electrode area is almost half. Accordingly, a relatively larger oxygen concentration is needed to obtain the limiting current at a low input voltage.

As mentioned above, from the aspects described above, the oxygen sensor of this Example is more advantageous than the comparative sensor to achieve miniaturization.

As described above, the first and second substrates (zirconia solid electrolyte) 1, 5 show oxygen ion permeability when heated to 350° C. or higher, enabling the pumping of oxygen. Accordingly, when the temperature of the gas atmosphere to be measured is 350° C. or higher, the sensor can be operated simply by placing it in this atmosphere. However, when the temperature of the gas atmosphere to be measured is lower than 350° C. (for instance, at room temperature), the sensor should be heated to 350° C. or higher.

A heating means for this sensor can be formed by coatin a Pt paste on the surfaces of the first and second substrates 1, 5 in areas where the Pt electrodes 3b, 6b are not formed. In this case, the heating means may be disposed on only one of the substrates. By this heating means, the oxygen sensor can be operated in a gas atmosphere at a considerably low temperature, for instance, at room temperature or lower. Since the oxygen sensor of this Example has a small heat capacity, it can be heated to an operable temperature with small electric energy.

Incidentally, in this Example, the first and second substrates 1, 5 having oxygen ion permeability are formed with a zirconia solid electrolyte prepared by dissolving $Y_2O_3$ as a stabilizer in $ZrO_2$, but the substrates are not restricted to this solid electrolyte. In addition to this zirconia solid electrolyte, such zirconia solid electrolyte made of $ZrO_2$ and containing CaO, MgO, $Yb_2O_3$, etc. as stabilizers may be properly used.

To achieve the miniaturization and low-temperature operation (350°–500° C.) of the oxygen sensor, the first and second substrates 1, 5 preferably has a thickness of 0.1–0.5 mm, and the diffusion pore 2 preferably has a pore diameter of 10–50 $\mu$m.

In the above Example, the first substrate 1 has one diffusion pore 2, but the present invention is not restricted to this structure. As long as it is satisfied that at least one of the first and second substrates 1, 5 has at least one diffusion pore 2, any other diffusion pores may be formed.

In a case where a plurality of diffusion pores 2 are formed, their sizes may be determined to achieve effective rate-determining function, taking into consideration the thicknesses of the first and second substrates 1, 5, average sizes of the first porous internal and external electrodes 3a, 3b and the second porous internal and external electrodes 6a, 6b, and their porosities. In addition, a plurality of diffusion pores 2 may have the same size or different sizes.

Further, in the above Example, both openings of the diffusion pore 2 in the first sensor element 4 are covered by first porous internal electrode 3a and the first porous external electrode 3b. However, an inner opening of the diffusion pore 2 may not be covered by the first internal electrode 3a, which is not directly exposed to the gas being measured so that it is less likely to be affected by dust.

The first internal and external electrodes 3a, 3b and the second internal and external electrodes 6a, 6b are not restricted to electrodes made of Pt. To achieve the function as catalytically active electrodes, metal materials such as Pt, Pb, Ag, Rh, Ir, etc., alloy materials of these elements, or mixed materials of these metal materials and at least one oxygen ion-permeable oxide material may be properly used.

These porous electrodes 3a, 3b, 6a, 6b may be formed not only by baking of pastes but also by sputtering, vacuum vapor deposition, plating, etc.

In these porous electrodes 3a, 3b, 6a, 6b, factors of determining their porosities, such as average particle size, average pore size, pore percentage may be determined as follows:

As far as the first sensor element 4 having the diffusion pore 2 is concerned, the average pore size of the first external electrode 3b need only be equal to or smaller than the pore diameter of the diffusion pore 2 in order that the first external electrode 3b functions as a filter for the diffusion pore 2. Further, to maintain its rate-determining function without decreasing the effective pore diameter of the diffusion pore 2, the average particle size of the first external electrode 3b need only be equal to or smaller than the pore diameter of the diffusion pore 2, and the pore percentage of the first external electrode 3b need only be at such a level that the electrode itself does not function as a layer for determining the oxygen supply rate. This is true of other electrodes, namely the second internal and external electrodes 6a, 6b, including a case where the diffusion pore 2 is formed in the second substrate 5 in the second sensor element 7.

In sum, in order that the electrodes 3a, 3b, 6a, 6b can function as filters for the diffusion pore 2, and in order that they can fully function as catalytically active electrodes with large three-phase interfaces between the first and second substrates 1, 5, the electrodes 3a, 3b or 6a, 6b and oxygen, thereby enhancing their oxygen pumping function, the above factors of the electrodes are preferably within the following ranges:

| | |
|---|---|
| Average particle size: | 1-3 μm |
| Average pore size: | 0.1-5 μm |
| Porosity: | 70-85% |

Further, the sealing means 8 is not restricted to glass, and any other sealing materials having good heat resistance, affinity to the first and second substrates 1, 5 made of a zirconia solid electrolyte, etc. may be properly used.

As described above in detail, the oxygen sensor of the present invention has the following advantages:

(1) Since the electrochemical oxygen pumping function and the rate-determining function and the sealing function are conducted by two sensor elements having substrates made of the zirconia solid electrolyte, the oxygen sensor can be miniaturized.

(2) Since the two substrates are provided with porous electrode, the three-plate interface between each substrate, the electrodes and oxygen are extremely large. Accordingly, a large oxygen pumping function can be provided, resulting in the reduction of input voltage to obtain a certain limiting current. It further achieves high response.

(3) By miniaturization and reduction of input voltage, the electric energy consumption of the oxygen sensor can be further decreased.

(4) Since the electrodes are constructed as porous structures, they function as filters for the diffusion pores. This contributes to the improvement of sensor characteristics and the extension of service life of the sensor.

(5) Since the electrode area is large, and since the substrate is fully thin, the oxygen pumping function and the rate-determining function can be fully maintained even at a low temperature by properly adjusting the opening ratio of the diffusion pore, so that the desired limiting current can be obtained. Accordingly, even in a low temperature operation condition, for instance, in working environment such as in tanks, where an oxygen-depleted state is to be detected at a relatively low temperature, a wide range of oxygen concentration can be detected at high accuracy and high response rate.

What is claimed is:

1. A limiting current-type oxygen sensor comprising:
    (a) a pair of sensor elements each comprising an oxygen ion-permeable substrate made of a zirconia solid electrolyte;
    (b) at least one diffusion pore provided in at least one of said substrates, which pore extends substantially along the thickness of said substrate for causing oxygen diffusion through said diffusion port to be a rate-determining step;
    (c) a sealing member for fixing said pair of substrates such that a closed chamber is defined between said substrates;
    (d) a pair of porous electrodes provided on both outer and inner surfaces of the substrate in each sensor element; and
    (e) a limiting current-detecting means connected between both inner electrodes and both outer electrodes.

2. The limiting current-type oxygen sensor according to claim 1, wherein said substrate has a thickness of 0.1-0.5 mm, and said diffusion pore has a diameter of 10-50 μm.

3. The limiting current-type oxygen sensor according to claim 1, wherein said internal and external electrodes have an average particle size of 1-3 μm, an average pore size of 0.1-5 μm and a porosity of 70-85%.

4. The limiting current-type oxygen sensor according to claim 2, wherein said internal and external electrodes have an average particle size of 1-3 μm, an average pore size of 0.1-5 μm and a porosity of 70-85%.

* * * * *

UNITED STATES PATENT AND TRADEMARK OFFICE
CERTIFICATE OF CORRECTION

PATENT NO.   : 4,950,380

DATED        : August 21, 1990

INVENTOR(S)  : Kurosawa et al.

It is certified that error appears in the above-identified patent and that said Letters Patent is hereby corrected as shown below:

Title page, Item [56], left hand column, under

"4,666,566  5/1987  Mizutani et al. .........204/1 T", insert

--FOREIGN PATENT DOCUMENTS

```
5748648     3/82    JAPAN   .....   27/46
5797439     6/82    JAPAN   .....   27/58
58210560   12/83    JAPAN   .....   27/58
5988653     5/84    JAPAN   .....   27/58
6024445     2/85    JAPAN   .....   27/58
5926895     7/84    JAPAN   .....   27/46--.
```

Signed and Sealed this

Ninth Day of June, 1992

Attest:

DOUGLAS B. COMER

Attesting Officer

Acting Commissioner of Patents and Trademarks